July 13, 1943. C. MALLERIN Plant Pat. 595
ROSE PLANT
Filed Jan. 19, 1943
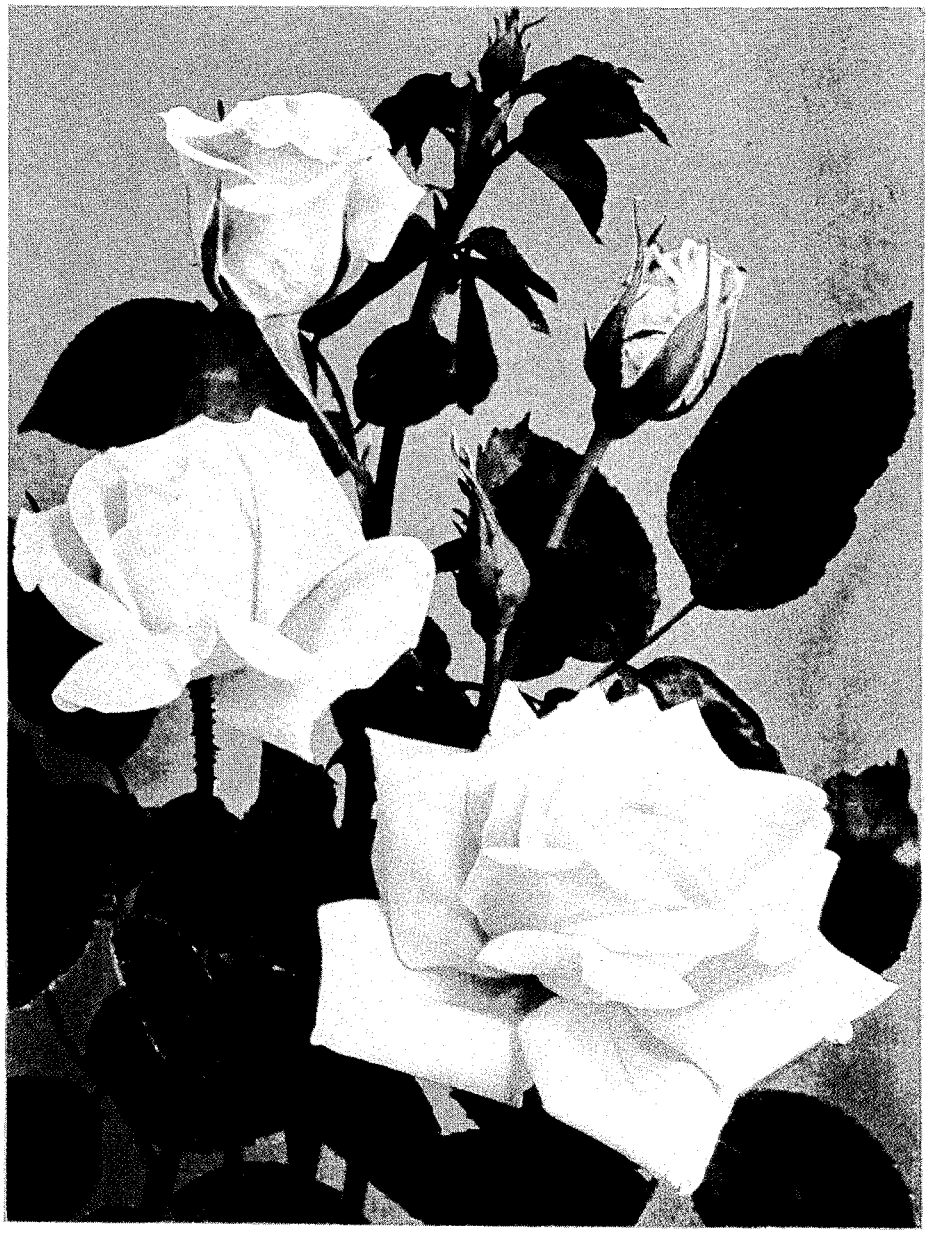
Inventor
Charles Mallerin
By Robb & Robb
Attorneys.

Patented July 13, 1943

UNITED STATES PATENT OFFICE

595

ROSE PLANT

Charles Mallerin, Varces, France, assignor to The Conard-Pyle Company, West Grove, Pa.

Application January 19, 1943, Serial No. 472,890

1 Claim. (Cl. 47—61)

The present invention relates to a new and distinct variety of hybrid tea rose plants, representing a most desirable improvement in its class because of its combination of those qualities that are most satisfactory and appealing in production.

The all around hardiness as an outdoor plant and suitability for purposes of cut flowers or garden decoration, combined with the size and color of its blossoms, as well as other of its features, mark this new variety as outstanding among any varieties now grown.

The following is a detail description of this new rose, color terminology having reference to Ridgway's Color Standard:

Type: Hardy; tall; bush; outdoor; seedling; for cut flowers and garden decoration.

Class: Hybrid tea.

Parentage: Seedling.

*Seed parent.*—Souv. de Melanie Soupert.

*Pollen parent.*—Nonin.

Propagation: Holds its distinguishing characteristics through succeeding propagations by budding, which is the only method employed up to the present time.

*Flower*

Locality where grown: West Grove, Pennsylvania.

Flowers borne: Singly and several to stem; on normal, medium long stems.

Quantity of bloom: Free; outdoors.

Continuity: Intermittent.

Fragance: Moderate; tea.

Bud:

*Peduncle.*—Medium long; medium heavy; erect; stiff; Rainette, Plate XXXI; numerous hairs, Garnet-Brown, Plate I.

*Before calyx breaks.—Size*—medium. *Form*—ovoid with an inconspicuous neck; with foliaceous appendages on the surface of the bud; with bristle-like foliaceous parts extending beyond the tip of the bud equal to one-half or more of its length.

*As calyx breaks.*—Lemon-Chrome, Plate IV, marked Nopal Red, Plate I.

*As first petal opens.—Size*—medium. *Form*—ovoid. *Color*—outside: Lemon-Chrome, Plate IV, shading upward to Pinard Yellow, Plate IV, at edge; inside—Lemon-Chrome, Plate IV, shading upward to Pinard Yellow, Plate IV, at edge.

*Opening.*—Opens up well.

Bloom:

*Size.*—When fully open, four inches to four and one-half inches.

*Petalage.*—Double (but the stamens not hidden); from twenty to twenty-five petals; arranged regularly.

*Form.*—Cupped; high center at first; becoming cupped; petals remaining at first loosely cupped rolled outward; becoming later, at maturity, very loosely rolled outward.

Petals: Thick; soft; with inside and outside satiny.

*Shape.—Outside*—obovate, with apex flat with one notch. *Intermediate*—obovate, with apex flat with one notch. *Inside*—obovate, with apex flat with one notch.

This description of a newly opened flower was made from a rose grown outdoors, in the month of August, 1941, at West Grove, Pennsylvania:

*Color.*—Outside petal: outside surface—Lemon-Chrome, Plate IV, shading to Baryta Yellow, Plate IV, at edge; inside surface—Lemon-Chrome, Plate IV, shading to Baryta Yellow, Plate IV, at edge. Intermediate petal: outside surface—Lemon-Chrome, Plate IV, shading to Baryta Yellow; Plate IV, at edge; inside surface—Lemon-Chrome, Plate IV, shading to Baryta Yellow, Plate IV, at edge. Inner petal: outside surface—Lemon-Chrome, Plate IV, shading to Baryta Yellow, Plate IV, at edge; inside surface—Lemon-Chrome, Plate IV, shading to Baryta Yellow, Plate IV, at edge.

This description was made from a rose that was open for three days in the month of August, 1941, at West Grove, Pennsylvania:

*Color.*—Outside petal: outside surface—Pinard-Yellow, Plate IV; inside surface—Pinard-Yellow, Plate IV. Inside petal: outside surface—Pinard-Yellow, Plate IV; inside surface—Pinard-Yellow, Plate IV.

*General color effect.*—Newly opened flower—Lemon-Chrome, Plate IV; three days open—Pinard-Yellow, Plate IV.

*Behavior.*—Drop off cleanly; fading Baryta-Yellow, Plate IV.

*Flower longevity.*—On bush in garden—two to three days in August. As cut roses grown outdoors—three to five days in August.

*Reproductive organs*

Stamens: Many; arranged irregularly partly about pistils, mixed with petaloids.
Filaments: Short and long; Peach-Red, Plate I; most with anthers.
Anthers: Medium large; Deep-Chrome, Plate III; open at once.
Pollen: Abundant; Zinc-Orange, Plate XV.
Pistils: Medium number.
Styles: Even; short; thin; bunched.
Stigma: Citrine, Plate IV.
Ovaries: All enclosed in calyx.
Hips: Short; flat; with inconspicuous neck: Oil Green, Plate V; smooth; walls thin.
Sepals: Permanent; moderately long; recurved.
Seeds: Very few; small.

*Plant*

Foliage:
*Leaves.*—Compound of three to seven leaflets; normal; moderately large; heavy; leathery.
*Leaflets.*—Ovoid; with apex mucronate; base obtuse; margin simply serrate.
*Color.*—*Mature:* upper surface—Cedar Green, Plate VI; under surface—Parrot Green, Plate IV. *Young:* upper surface—Oil Green, Plate V, suffused Garnet-Brown, Plate I; under surface—Garnet-Brown, Plate I, suffused Oil Green, Plate V.
*Rachis.*—Medium heavy. Upper side—prickly; under side—thorny.
*Stipules.*—Moderately long; moderately narrow; with moderately long points turning out at an angle of more than 45°, recurved toward the stem.
*Disease.*—Resistant to mildew and blackspot.

Growth:
*Habit.*—Bushy; upright; much branched.
*Growth.*—Vigorous.
*Canes.*—Medium heavy.
*Main stems.*—Dull Olive-Green, Plate IV. *Thorns*—several; short; hooked downward; with long narrow base. *Prickles*—none. *Hairs*—none.
*Branches.*—Dull Cerro-Green, Plate V. *Thorns*—several; medium long; hooked downward; with narrow base. *Prickles*—none. *Hairs*—none.
*New shoots.*—Bright Cerro-Green, Plate V, suffused Morocco Red, Plate I. *Thorns*—several; medium long; hooked downward; with long narrow base. *Prickles*—none. *Hairs*—none.

I claim:

A new and distinct variety of rose plant, characterized as to novelty by general habits of growth, hardiness, color and form of flowers throughout their different stages of development, and color combination of foliage, substantially as shown and described.

CHARLES MALLERIN.